(12) United States Patent
Chauhan

(10) Patent No.: US 11,989,877 B2
(45) Date of Patent: May 21, 2024

(54) METHOD AND SYSTEM FOR ANALYSING IMAGES OF A RETINA

(71) Applicant: MACUJECT PTY LTD, Kew (AU)

(72) Inventor: Devinder Singh Chauhan, Kew (AU)

(73) Assignee: Macuject Pty Ltd (AU)

( * ) Notice: Subject to any disclaimer, the term of this patent is extended or adjusted under 35 U.S.C. 154(b) by 547 days.

(21) Appl. No.: 17/273,847

(22) PCT Filed: Aug. 28, 2019

(86) PCT No.: PCT/AU2019/050915
§ 371 (c)(1),
(2) Date: Mar. 5, 2021

(87) PCT Pub. No.: WO2020/056454
PCT Pub. Date: Mar. 26, 2020

(65) Prior Publication Data
US 2021/0319556 A1 Oct. 14, 2021

(30) Foreign Application Priority Data
Sep. 18, 2018 (AU) ................................ 2018903511

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/30* (2017.01); *G16H 70/60* (2018.01);
(Continued)

(58) Field of Classification Search
CPC . G06T 7/0012; G06T 7/11; G06T 7/30; G06T 2207/10101; G06T 2207/20081;
(Continued)

(56) References Cited

U.S. PATENT DOCUMENTS

2012/0150029 A1 6/2012 Debuc
2015/0062590 A1 3/2015 Bagherinia
(Continued)

FOREIGN PATENT DOCUMENTS

WO  WO-2016177722 A1 * 11/2016 ........... A61B 3/0025
WO  WO-2018034465 A1 *  2/2018 ............. A23K 10/30

OTHER PUBLICATIONS

International Search Report and Written Opinion corresponding to International Patent Application No. PCT/AU2019/050915, dated Sep. 9, 2019.
Chen et al., "Automated drusen segmentation and quantification in SD-OCT images." Medical Image Analysis, 2013. vol. 17, No. 8, pp. 1058-1072.

*Primary Examiner* — Dhaval V Patel
(74) *Attorney, Agent, or Firm* — McAndrews, Held & Malloy, Ltd.

(57) ABSTRACT

Provided is a method and system for analysing images of a retina captured by an Optical Coherence Tomography (OCT) scanner. In some examples, an image of a retina of a patient from an OCT scanner is received; boundaries between layers are segmented for each of the pixels; the layers are determined using the segmented boundaries; regions of pathology are segmented for each of the pixels; a location of the regions of pathology are determined with respect to the determined layers using the segmented regions; the regions of pathology are determined using the segmented regions and the determined location of the regions; a property of the regions of pathology are determined using the segmented regions; results of determinations of the regions of pathology and the property of the regions to derive an assessment are analysed; and the assessment are output.

17 Claims, 2 Drawing Sheets

(51) Int. Cl.
*G06T 7/30* (2017.01)
*G16H 70/60* (2018.01)

(52) U.S. Cl.
CPC ............... *G06T 2207/10101* (2013.01); *G06T 2207/20081* (2013.01); *G06T 2207/20084* (2013.01); *G06T 2207/30041* (2013.01)

(58) Field of Classification Search
CPC . G06T 2207/20084; G06T 2207/30041; G06T 7/0014; G06T 7/337; G06T 7/12; G16H 70/60; A61B 3/10; A61B 3/0025; A61B 3/1005; A61B 3/102; A61B 3/12; A61B 3/0058; A61B 5/0066; A61B 5/4842; A61B 5/489; A61B 5/725; A61B 5/7253; A61B 5/7267; A61B 2576/02
See application file for complete search history.

(56) References Cited

U.S. PATENT DOCUMENTS

| | | | |
|---|---|---|---|
| 2017/0119242 A1 | 5/2017 | Jia et al. | |
| 2018/0132725 A1 | 5/2018 | Vogl et al. | |
| 2018/0146850 A1* | 5/2018 | Fernandes Da Cunha-Vaz | A61B 3/1225 |
| 2018/0344806 A1* | 12/2018 | Borodic | A61P 27/02 |
| 2019/0279358 A1* | 9/2019 | Schaal | G06T 7/143 |
| 2019/0328808 A1* | 10/2019 | Ma | A61P 27/02 |
| 2020/0069175 A1* | 3/2020 | Kumagai | A61B 3/0025 |
| 2020/0075155 A1* | 3/2020 | Huang | G06T 7/0012 |
| 2020/0211710 A1* | 7/2020 | Do | G16H 50/30 |

* cited by examiner

METHOD AND SYSTEM FOR ANALYSING IMAGES OF A RETINA

The application is a U.S. National Phase Entry of International Application No. PCT/AU2019/050915 filed on Aug. 28, 2019, designating the United States of America. The present application claims the benefit of the above-identified application and Australian Patent Application No. 2018903511 filed on Sep. 18, 2018, both of which are hereby incorporated by reference herein in their entirety.

TECHNICAL FIELD

The present invention relates to a method of analysing images of a retina captured by an Optical Coherence Tomography (OCT) scanner. In particular, but not exclusively, the method uses a processor configured to implement the steps of receiving images of a retina of a patient captured by an OCT scanner, determining layers of the retina, determining regions of pathology of the retina, and analysing the regions of pathology to derive an assessment of the retina of the patient. The assessment of the retina enables, for instance, the treatment of the patient's retina to be evaluated and determined.

BACKGROUND OF INVENTION

The inner coats of the human eye are responsible for vision. Working from the outside inwards, these coats include: the choroid; the retinal pigment epithelium; and the retina itself. Diseases affecting these, and adjoining, coats can have a significant effect on vision. The choroid is comprised of a dense plexus of blood vessels, which supply oxygen and nutrients to the outer retina and retinal pigment epithelium. The inner aspect of the retina is also vascularised; these retinal blood vessels supply the inner aspect of the retina.

Many diseases affecting the eye, particularly those with a vascular component to their pathology, cause disruption of the retina and choroid, with resultant visual effects. These diseases may be primarily ocular or systemic. Examples of these include age-related macular degeneration (AMD), diabetic retinopathy and retinal vein occlusion.

The integrity of the blood vessel walls and the flow within the blood vessels govern the mechanisms by which diseases affecting blood vessels cause harm to vision. Reduced or absent blood flow in the retina may result in retinal and anterior segment neovascularisation, such as in diabetic eye disease. Damage to retinal blood vessel walls can also result in haemorrhage within the retina and ischaemia; examples include retinal vein occlusion and diabetic eye disease.

The most commonly treated conditions affecting the macula, however, relate to leaky blood vessels. That is, damage or immaturity of retinal or choroidal blood vessel walls results in a net outflow of fluid from a capillary bed. Any disruption to blood vessel walls, particularly to the components of the blood retinal barrier, can result in a net outflow of fluid from capillary beds into tissues. This leads to the development of a swelling of the retina and is commonly seen as macular oedema. Macular oedema can be either symptomatic or asymptomatic; the presence and degree of symptoms depends on a number of factors. These include the location and extent of the macular oedema, as well as its effect on intracellular and extracellular matrix, particularly with respect to metabolic and visual function.

The retina is not homogeneous, consisting of several well-described layers on histological sections. Whilst the anatomical layering of the retina appears to be orientated such that the layers are essentially organised concentrically in the eye and roughly parallel to the surface of the retina, the functional organisation of the retina is orthogonal to this plane. That is, each of the histological layers is comprised primarily of a single cell or cell component type. However, there are multiple interconnections between layers, primarily synaptic, but also neuronal, glial or structural. The disruption of macular function (vision) by the presence of macular oedema is probably due to both physical deformation/disruption and biochemical effects on individual cells, the retinal layers and their interconnections.

The fovea is the central part of the macula, with the highest concentration of photoreceptors. Disease affecting the centre of the fovea generally has a greater impact on visual function.

The constituents of the fluid that leaks from blood vessels include water, protein, lipids, platelets and red and white blood cells. In addition, differential leakage and reabsorption may result in possible concentration or dilution of leaked blood constituents. It is believed that extracellular fluid diffuses and spreads within the retina within retinal layers as well as extending into neighbouring layers. This distribution is likely to be influenced partly by the orientation of structural components within the retina as well as mechanical, extracellular and intercellular barriers to free flow of fluid. As a consequence of these constraints, there is deformation and disruption of the topology of individual layers of the retina and choroid, as well as their boundaries and interfaces. The location and extent of these changes influences vision both in the short and long term.

On an histological basis, macular oedema can be seen as either a diffuse thickening of the whole macula, layers within it or cystoid spaces. The latter are simply collections of fluid, whereas the surrounding areas of diffuse thickening include areas of cellular abnormality and extracellular interstitial fluid that has not coalesced to form a cystoid space. It is likely that diffuse macular oedema surrounds cystoid spaces and is an earlier sign of vascular leakage. Indeed, diffuse macular oedema is likely to be a more sensitive and specific sign of leakage, cystoid spaces only being present once the leakage has exceeded the threshold for pooling of extracellular fluid or if there has been structural collapse. The development of diffuse macular oedema often precedes cystoid macular oedema. It is important, therefore, to distinguish between diffuse intraretinal fluid (DIRF) and focal, or cystoid, intraretinal fluid (FIRF).

Optical coherence tomography (OCT) is a non-invasive imaging technique used to generate three-dimensional cross-sectional scans of retina and other tissues. Spectral domain and swept source OCT are now of significantly higher resolution than previous iterations of OCT. It is therefore possible readily to recognise, segment and measure individual layers and combinations thereof using this technology. In spite of this, OCT images are not the same as histologic cross sections. Whilst there is a strong correlation between histological and OCT images, the latter are generated as a result of the optical perturbations of the incident light on a tissue, rather than simply its cellular constitution and organisation; the optical properties of superficial layers influence the imaging of deeper layers. In use, an OCT scanner generates a set of A-scans across a retina to generate a cross-sectional reconstruction of the retina known as a B-scan. Adjacent B-scans are lined-up in order to produce a three-dimensional scan, sometimes known as a macular cube.

The intensity of OCT signals relates to many optical properties of the tissue; interfaces between layers of different refractive indices, the optical density and backscattering properties of individual cells, their organelles and their organisation within layers of the retina all influence signal intensity and the intensity of signal from deeper tissues. It has been established that bodies of clear serous fluid generate a low signal. In an example of existing OCT scans of the macula of an eye, a focal region of pathology in the form of focal intraretinal fluid (FIRF) can be seen as distinct and discrete dark spaces that are readily identified on inspection by most observers and have been detected, delineated and labelled by several automated and artificial intelligence (AI) programs. Diffuse intraretinal fluid (DIRF), however, has been, by contrast, difficult reliably to identify and label, both by expert image graders and AI software. Also, quantification of DIRF has not been achieved reliably enough to inform clinical decision-making with respect to assessment for treatment for, say, macular oedema. That is, existing segmentation techniques, to determine regions of pathology of the retina, such as DIRF, may have too low accuracy or may be too unreliable to be used to clinically assess the retina of a patient.

The above discussion of background art is included to explain the context of the present invention. It is not to be taken as an admission that any of the documents or other material referred to was published, known or part of the common general knowledge at the priority date of any one of the claims of this specification.

SUMMARY OF INVENTION

One aspect of the present invention includes a method of analysing images of a retina captured by an Optical Coherence Tomography (OCT) scanner, the method using a processor configured to implement the steps of: receiving an image of a retina of a patient from an OCT scanner, the image having a plurality of pixels; segmenting boundaries between layers of the retina for each of the pixels; determining the layers of the retina using the segmented boundaries; segmenting regions of pathology of the retina for each of the pixels; determining a location of the regions of pathology with respect to the determined layers of the retina using the segmented regions; determining the regions of pathology using the segmented regions and the determined location of the regions; determining a property of the regions of pathology of the retina using the segmented regions; analysing results of determinations of the regions of pathology and the property of the regions to derive an assessment of the retina of the patient, wherein the property of the regions of pathology includes an indication of the volume of the regions of pathology; and outputting the assessment of the retina of the patient.

Preferably, the method further includes storing the image of the retina of the patient in a memory, receiving a subsequent image of the retina of the patient, and storing the subsequent image of the retina of the patient in the memory. Further, the assessment is also stored in a memory, and the method includes comparing the assessment with a subsequent assessment of the subsequent image of the retina of the patient to derive a progress assessment for the patient.

An assessment of the retina may include the diagnosis of a disease such as: macular degeneration, diabetic retinopathy and retinal vein occlusion. The progress assessment may include an assessment on the progress of one these diseases following a treatment protocol being applied to the retina of the patient.

Historically, for example, treatment protocols that were used for intravitreal injections of anti-VEGF agents were very simple, consisting of monthly injections. Subsequently, agents have been introduced for which the frequency of injection has been lower, but the duration of effects of the drug, assessed using OCT scans, can be variable. That is, some eyes require injections every four weeks, but others require injections once every 12 weeks or more. Optimally, the treatment of exudative macular disease is individualised for the patient such that the least number of injections results in the greatest long-term vision and least macular oedema. That is, the choice of drug, dose and interval between treatments is tailored to the individual eye. These decisions are currently made by ophthalmologists using information from measurements of patients' vision, changes in symptomatology and, most importantly, visual inspection of OCT images. OCT scans are not only more objective, but also more sensitive to change than the vision measurements and reported vision. The treating ophthalmologist generally assesses the OCT scans for the presence or absence of fluid, changes in comparison with previous scans and the rates of any changes.

In respect of the above method, the progress assessment of the retina can be used to determine the efficacy of a treatment protocol. That is, the method may assess a patient's OCT scans of their retina throughout their treatment period and these may be used to recommend a drug, treatment interval, potential additional tests required, potential visual outcome in the long-term, etc.

Patients' retinal OCT scans are acquired by an OCT scanner (which may be in the doctor's clinic, a hospital, a public place or even in the patient's home) and the images of the OCT scans are analysed as per the above method. Alternatively, the OCT scans may be transmitted securely to the cloud, and then analysed.

Preferably, the layers of the retina include: retinal pigment epithelium layer; layer of inner and outer segments; outer limiting layer; outer nuclear layer; outer plexiform layer; inner nuclear layer; inner plexiform layer; ganglion (cell) layer; layer of nerve fibres; and inner limiting layer.

In an embodiment, the regions of pathology include focal regions of pathology and non-focal regions of pathology. Preferably, the focal and the non-focal regions of pathology include: subretinal fluid SRF; focal intraretinal fluid (FIRF); diffuse intraretinal (DIRF); drusen; reticular pseudodrusen, subretinal hyper-reflective material intraretinal hyper-reflective foci, geographic atrophy; retinal pigment epithelial detachments; atrophic cysts; photoreceptor disruption/space; and outer retinal tubulation.

In an embodiment, the method further includes determining a layer topography of the retina using the segmented boundaries and comparing the layer topography of the retina to an expected layer topography of a retina without any regions of pathology. Also, the method further includes determining a distribution of the non-focal regions of pathology in the retina by combining the expected layer topography with the segmented regions of pathology.

Preferably, the property of the regions of pathology further includes: size of the regions; shapes of the regions and a count of the regions.

In an example, the detection, characterisation and quantification of DIRF is particularly significant when assessing the therapeutic effect of a treatment protocol. That is, as the DIRF develops before FIRF and is probably last to disappear, it is potentially one of the most sensitive parameters for determining the onset and diminution of therapeutic effect of therapeutic agents. In the example, the method determines the focal region of pathology in the form of DIRF using the segmented regions and its determined location with respect to the determined layers of the retina and with respect to the fovea. An indication of the volume of the DIRF is determined and the method derives the assessment of the retina based on the DIRF and its volume. In other embodiments, the two-dimensional and three-dimensional size, shape, contour, and count of the DIRF is considered by the method.

In an embodiment, the method further includes determining a thickness of the layers of the retina using the segmented boundaries in a neural network model. For example, the neural network model is a R-net model. The thickness of the layers of the retina can further be determined using a distribution of layer thicknesses derived from known layer thicknesses of a population. Also, the thickness of the layers of the retina using a distribution of layer thickness shapes can further be derived from known layer thickness shapes of a population.

In an embodiment, the method further includes segmenting boundaries between layers using adjacent B-scans of images of the retina received from the OCT scanner. As mentioned, the B-scans are cross sectional reconstructions of the retina and adjacent B-scans of the retina are reconstructed to form a macular cube.

In an embodiment, the method further includes pre-processing the image and the subsequent image of the retina to normalise for systematic differences in the images produced by different OCT scanners. Particularly, the method further includes transforming the image and the subsequent image of the retina to normalise parameters of the image and the subsequent image. These parameters include, for instance, contrast and scaling.

In the embodiment, the method further includes registering the image and the subsequent image of the retina into a standard coordinate space. The method may further include aligning the subsequent image into the standard coordinate space using a fundus image of blood vessels of the retina received from the OCT scanner. Alternatively, or additionally, the method further includes classifying, using a fovea finding classifier, each of the pixels of the image into fovea and retina classifications; and identifying the centre of the fovea of the retina in the image based on results of the fovea and retina classifications of the pixels. The image and the subsequent image are then aligned into the standard coordinate space using the centre of the fovea.

Pathological changes in the shape and topology of individual layers of the retina, or clinically relevant combinations of layers, and the relationship of these to the location and shape of the fovea are likely to be of relevance to both treatment decisions and prediction of treatment outcome. Determining the location of the centre of the fovea on OCT scans of normal maculas or those with minimal pathological disruption is less difficult to perform than in the presence of advanced disease. In the embodiment, the normalised images are used to assist the fovea-finding classifier. Having located the fovea, this facilitates longitudinal follow-up as well as prediction and optimisation of treatment outcomes for the patient. This approach can be applied retrospectively so that, if the fovea is more reliably found in a macula from one or more of a series of scans from the same eye, that location of the fovea can be applied to other scans for longitudinal comparisons.

For example, images of the retina are analysed according to the method and volume of each of the different collections of fluid forming the regions of pathology in the retina as well as mathematical and representative descriptions/measurements of the layers within the macula and choroid of the retina, such as diffuse and focal IRF and subretinal fluid (DIRF, FIRF and SRF), are used to derive the assessment of the retina. As mentioned, a comparison of the most recent assessment with a previous one is performed. In the case of OCT scans acquired in the clinic or the doctors' office, this may be once a month or less frequently, governed by the frequency of attendance of the patient. In the case of the OCT scanners in the community or in the patient's home, scans may be acquired more frequently. In any event, the resultant progress assessment may be used by a clinician to inform the following decisions:

Should an injection be performed today?
Which drug should be injected today?
When should the next injection be performed?
Which drug should be injected next time?
Are any further tests required?
Should any different diagnoses be entertained?
Are there any other problems today that need to be addressed, potentially through examination and review by the doctor?

If OCT scans are acquired in between visits to the doctor (injections), then further questions will arise:

What is the nature and extent of therapeutic effect of the most recent injection?
Is the rate of change of OCT parameters indicative of future response to the same drug?
Is the rate of change of OCT parameters indicative of future response to another drug?
What is the likely long-term and short-term visual outcome with the current drug?
Should the patient have any change in their management prior to the next planned visits to the doctor?
What is the likelihood of other macular disease (geographic atrophy, for example) occurring?
How many injections is the patient is likely to require in the future?
How often are these injections likely to be necessary?
If the patient stops injections, is the condition is likely to recur and, if so, when?

Further, a comparison of the present assessment may also be compared with previous assessments throughout the patient's visits and there may be a regular comparison with the initial assessment if the patient's condition worsens. There is also a comparison with the assessment and possibly the OCT scans from times when the patient was on a different drug and different injection frequency (interval). The treatment protocol also takes into account patients returning earlier than planned for injections and also later than planned. In addition, flexibility exists around patient choice and doctor choice with respect to performing both injections at the same time, even separating the two etc. is incorporated into the protocol such that the protocol differs from published ones in which real world evidence (RWE) and experience is not incorporated.

Another aspect of the present invention includes a system for incorporating individual practitioner preferences for several variables in the protocol, including interval increments, order of choice of drugs and protocol choice for different drugs.

Another aspect of the present invention includes software for use with a computer including a processor and memory for storing the software, the software including a series of instructions executable by the processor to carry out the method as claimed in any one of the preceding claims Another aspect of the present invention includes a system for analysing images of a retina, the system including: an Optical Coherence Tomography (OCT) scanner configured to capture images of a retina, each of the images having a plurality of pixels; a processor in data communication with the OCT scanner; a memory; and software resident in the memory accessible to the processor, the software including a series of instructions executable by the processor to configure the processor to: receive an image of a retina of a patient from the OCT scanner; segment boundaries between layers of the retina for each of the pixels; determine the layers of the retina using the segmented boundaries; segment regions of pathology of the retina for each of the pixels; determine a location of the regions of pathology with respect to the determined layers of the retina using the segmented regions; determine the regions of pathology using the segmented regions and the determined location of the regions; determine a property of the regions of pathology of the retina using the segmented regions; analyse results of determinations of the regions of pathology and the property of the regions to derive an assessment of the retina of the patient, wherein the property of the regions of pathology includes an indication of the volume of the regions of pathology; and output the assessment of the retina of the patient.

BRIEF DESCRIPTION OF DRAWINGS

Embodiments of the invention will now be described with reference to the accompanying drawings. It is to be understood that the embodiments are given by way of illustration only and the invention is not limited by this illustration. In the drawings.

DETAILED DESCRIPTION

Figure 1:
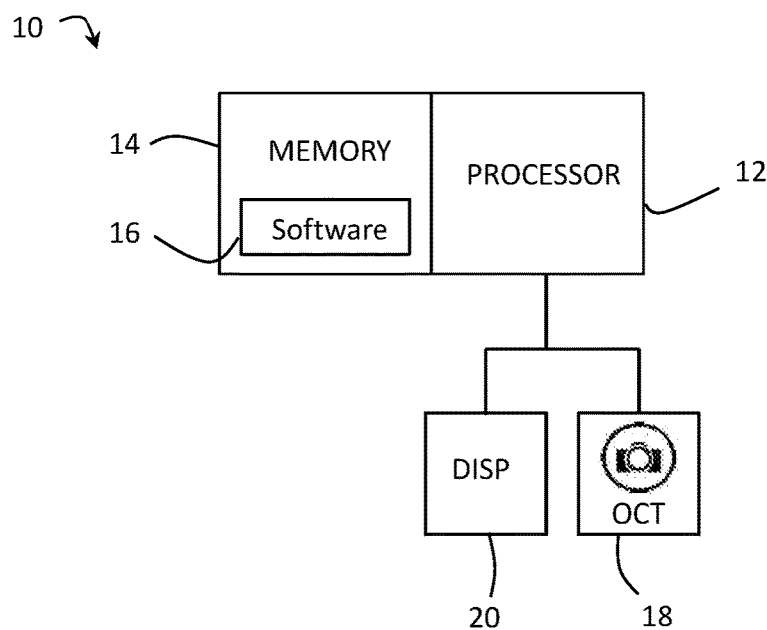
FIG. 1 is a schematic of a system for analysing images of a retina according to an embodiment of the present invention.

A system 10 for analysing images of a retina according to one embodiment of the present invention is shown in FIG. 1. The system 10 includes a computer having a processor 12 and a memory 14. The memory 14 contains software 16, resident thereon, including a series of instructions executable by the processor 12 to configure the processor 12 to perform a number of steps to analyse images of a retina.

The system 10 includes an Optical Coherence Tomography (OCT) scanner 18 configured to capture the images of a retina, whereby each of the images has a plurality of pixels. The OCT scanner 18 may communicate with the processor 12 of the computer via a physical or wireless interface, or may form a single apparatus with the computer. In any case, the OCT scanner 18 is used for capturing images of a patient's retina.

Images of the retina may be stored in the memory 14 or on a remote server (not shown), and these images are accessible to the processor 12 for analysis. To do so, the processor 12 is configured by the software 16 to first receive the images and then to segment boundaries between layers of the retina for each of the pixels in the images. The processor 12 is further configured to determine the layers of the retina using the segmented boundaries, segment regions of pathology of the retina for each of the pixels, such as Diffuse Intraretinal Fluid (DIRF), determine a location of the regions of pathology with respect to the determined layers of the retina using the segmented regions, determine the regions of pathology using the segmented regions and the determined location of the regions, and determine volume of the regions of pathology of the retina using the segmented regions. The results of determinations of the regions of pathology and the volume of the regions are then used to derive an assessment of the retina of the patient. The assessment of the retina of the patient is then outputted to, for example, a display 20.

As mentioned above, the volume of the regions of pathology is one of a number of properties of the regions of pathology that are used to derive the assessment. Other properties include a two-dimensional size of the focal region of pathology, shape, and count of the regions.

Figure 2:
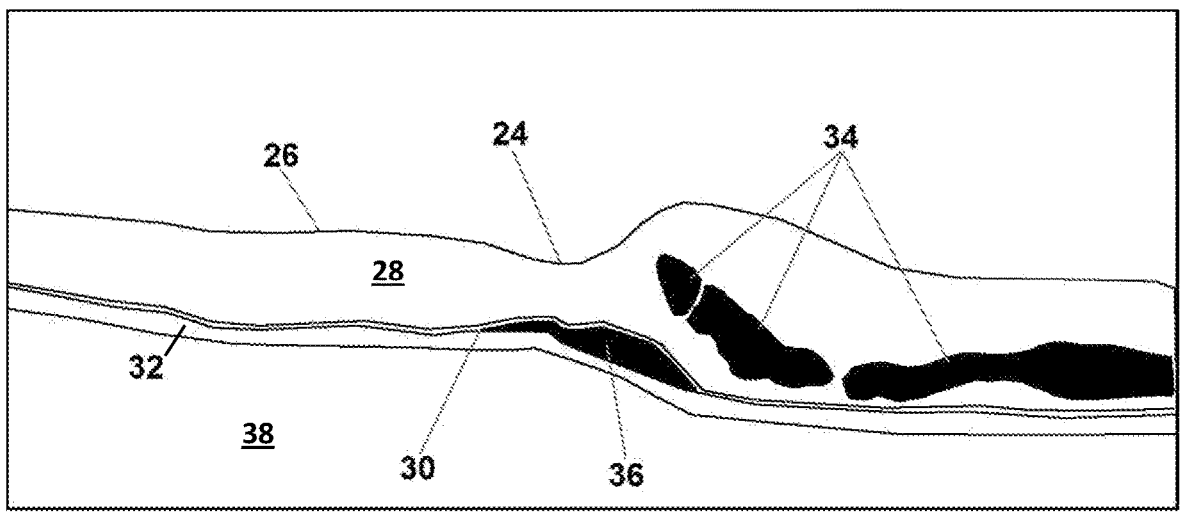
FIG. 2 is a representation of an image of a retina captured by an Optical Coherence Tomography (OCT) scanner.

FIG. 2 shows a simplified B-scan image 22 from the OCT Scanner 18 of a macula of a retina of a patient. Here it can be seen that the retina has a fovea 24 located fairly centrally within the image 22 of the macula of the retina, and four layers defined by boundaries. The first boundary defines the surface of the macula 26. The first layer 28, beneath the surface 26, is a simplified representation of the whole of the neurosensory retina 28, the second layer is a representation of an outer surface of a neurosensory retina including a photoreceptor layer 30, and the third layer is the retina pigment epithelium layer 32. Beneath the retina pigment epithelium layer 32 is the choroid 38. The first layer 28 and the second layer 30 have regions of pathology located within and under, respectively. Specifically, the first layer 28 has intraretinal fluid 34 trapped within it. The second layer 30 also has subretinal fluid 36 trapped under it. The system 10 analysing this image would, using the steps described above, determine the four layers 28 30 32 38 of the retina using the boundaries of the layers, determine locations of the intraretinal fluid 34 and subretinal fluid 36 with respect to the layers 28 30 32 38, and thus determine the intraretinal fluid 34 as XIRF and subretinal fluid 36 a Y-SRF. The system 10 would then determine the volume of the intraretinal fluid 34 and the subretinal fluid 36, and then use this to derive an assessment of the retina.

In more specific embodiments of the present invention, the system 10 can be described as a pipeline for OCT image data processing and predictive modelling that operates in several stages. At a high level, the stages of the processing pipeline first include the steps associated with loading image data. As mentioned, the image data is produced by the OCT scanner 18 and is read into the data processing pipeline. Image data is created by an OCT scanner and transferred to a general purpose computer (with GPU), which is either contained in the same device as the OCT scanner or exists as a separate device on the same local network as the OCT scanner or remotely in a cloud computing environment. Image data is typically represented as a binary file containing a single flattened array of pixel intensities. This array is reshaped into a cuboid which is indexable by coordinates in 3-dimensional space. The dimensions of the cuboid are dependent on the specific OCT scanner used to create the image, as well as the parameters of the scan performed.

The loaded images may be transformed in order to normalise for systematic differences in the images produced by different OCT scanners. OCT images captured by different OCT scanners have different characteristics in terms of their resolution, contrast, signal-to-noise ratio, etc. To improve compatibility with images generated by a range of different OCT scanners, a set of mechanisms for normalizing scans and making models robust to differences in the characteristics of different OCT scanner models are used. These methods include: normalizing scans with respect to contrast and scaling, performing data augmentation to vary the characteristics of training images, and fine-tuning machine learning models on a set of real training examples collected from the different OCT scanner models types.

The images are then registered to a common coordinate system so that the presence of a focal region of pathology, generally a fluid, at specific locations of the retina can be compared across scans taken from patients at different times and even across patients and OCT scanners. This pre-processing of images is used to standardize the appearance of images before the images are passed to the machine learning systems of the system 10.

Localisation of important structures in the retina by the machine learning systems is then performed, using an ensemble of images, acquired by a range of modalities, including OCT and complementary methods. Fovea finding and segmentation is accomplished with the aid of a dataset of OCT scans, as well as en-face fundus images, in which the fovea position has been annotated by clinicians skilled in the interpretation of retinal images. The en-face image is acquired at the same time as the OCT scan, using scanning laser ophthalmoscopy (SLO). The en-face image shows the surface of the fundus, with blood vessels and the optic nerve clearly visible due to their difference in reflectance. As en-face images are acquired at the same time the OCT scan data, alignment between both image types is typically very good, and SLO data can thus be used as an additional source of retinal morphology data to guide OCT scan analysis. The system 10 incorporates fovea location knowledge arising from the annotated fovea dataset, including SLO images. This information is used during training and embodied as a set of weights in the fovea finding classifier. By incorporating fovea location data created using diverse retina images by experienced clinicians, performance of the system on pathological examples is potentially improved, with the fovea finding classifier likely to exhibit better ability to cope with patients' unique retinal morphology, compared to previous approaches relying on classical layer-segmentation algorithms.

The system 10 includes methods to align OCT scan data from the same patient acquired at different times in the patient history, or by dissimilar imaging modalities. To this end, to achieve accurate registration, we focus on the geometry of blood vessels, (which are visible in all the en-face imaging modalities considered) to select and describe keypoints.

The en-face OCT image is aligned to the OCT macular cube and shows the retinal blood vessels; hence it serves as the anchor point for registration of the en-face imaging modalities to the OCT macular cube and HD raster scans.

In order to segment blood vessels for en-face registration, the images are pre-processed to enhance the appearance of blood vessels relative to other features of the retina. For example, for fundus images all colour channels except green may be dropped, since the green channel provides the highest contrast between blood vessels and background. Additional filters and transformations may be applied to enhance the appearance of the blood vessels, with parameters tuned for specific imaging modalities (e.g. fundus image, en-face OCT image, fundus autofluorescence image, etc).

After filtering, segmentation of blood vessels may occur in one of two ways; using edge-detection methods, or through a deep segmentation model such as U-Net.

Edge-detection methods used to segment blood vessels may include Gaussian filtering, ridge detection, matched filtering, steerable filtering, bottom-hat transformation and other related techniques. In order to segment the vascular structure using U-Net, a collection of ground-truth blood vessel masks are created by human experts for each imaging modality. These masks are used to train multiple U-Net models (one for each en-face imaging modality) to create blood vessel masks corresponding to the en-face input images.

Following segmentation, post-processing is carried out, in order to correct defects in the blood vessel segmentation map; for example either because the segmentation algorithm failed to detect a region of vessel or because it introduced a spurious edge detection where no vessel was present. Several approaches are available to perform this post processing step, including shortest path graph-search methods to connect disconnected sections of the vascular tree, and conversion segmentation maps to a set of key points.

Key point creation from blood vessel segmentation maps allows blood vessel maps, and hence fundus images, to be aligned, even in cases where pathology or ageing alters the overall appearance of the fundus significantly.

The keypoint descriptors may be augmented with further features to improve the robustness of the correspondence, e.g. measurement of vessel length and angle within frames of differing sizes around the feature point, or partial intensity-invariant feature descriptors.

The alignment can be further optimized by applying a geometric transformation to the keypoints, under the assumption of a spherical eye. This involves the estimation of a 6-parameter camera pose transformation (3 translation parameters and 3 orientation parameters). By estimating relative camera position for each of the two captured images, alignment of the images is improved, and the method is more robust to variation in camera setup between instruments.

Transformation under the spherical eye model and estimation of camera pose are accomplished by defining the alignment as an optimization problem, with a loss function defined to measure distances between corresponding keypoints. The loss is optimised using particle-swarm optimisation, initialized around the random sample consensus (RANSAC) pose estimate. Once the particle swarm optimization has converged to a final estimate of the alignment transformation, that transformation is applied to the image to be aligned. Particle swarm optimization has the advantage that large search spaces can be covered efficiently, increasing the chance that an optimal alignment may be found in cases where fundus images diverge significantly.

A key aspect of the system 10 is deriving an assessment of the retina which may be the diagnosis of a disease and then tracking the progression of the patient's disease. This will enable the system 10 to make predictions about the patient's future condition and about the best possible interventions based not only on the current features of the patient's disease but also on its change over time.

The features of disease (macular degeneration, diabetic retinopathy and retinal vein occlusion) to be considered are also related to the position of the fovea. These features include the volume of fluid present in different compartments and forms and the shape and dimensions of individual retinal layers and combinations thereof. In order to describe and track changes in these features, the system 10 implements steps for foveal finding and for image registration into a standard coordinate space.

Properties of the detected regions of pathology, including volume, size, signal characteristics and location, as well as changes from previous scans, are extracted from the segmented images. The extracted features are then used to make predictions about the patient's retina disease progression and optimal treatment choices, as well as in populations.

For fovea finding, the system 10 uses a fovea finding classifier. The first step of the classification involves classifying B-scans according to whether the centre of the fovea is contained within the B-scan or not. For this purpose, a neural network classifier is trained to predict a binary output variable that indicates whether a B-scan contains the centre of the fovea. The network takes as input a series of consecutive B-scans that may or may not have been pre-segmented using a layer segmentation model, and the target variable indicates whether the central scan in the slice contains the centre of the fovea. The network used in this step is a typical convolutional neural network with either 2d or 3d convolutions followed by a fully-connected layer which calculates a single output variable.

This classifier may be trained on the raw B-scans captured by the OCT scanner 18, or it may be trained on images segmented by the layer segmentation system described below.

The second stage involves finding the location of the fovea centre in the selected B-scan. This can be accomplished by a regression network (CNN followed by FC layer) that outputs the location of the fovea centre relative to the width of the B-scan. The training data for fovea finding may be collected by marking the centre of the fovea on a reconstructed fundus image. Foveal finding may also be accomplished by using a regression network like the one described for the second stage on reconstructed fundus images.

When an OCT scan contains severe disease, the fovea may be hard to locate using B-scans only. In this case, image registration on past scans may be used to infer the location of the fovea in the diseased scan. Another approach is to fit a parametric model (e.g. penalized B-spline surface) to the retinal boundaries of one diseased and one healthy eye (if available), and then align the surfaces in the healthy regions only, thus 'registering' the diseased eye to a reflected image of the healthy one, and allowing the location of the fovea to be inferred from the healthy eye.

The boundaries between retinal layers are segmented and identified on a per-pixel basis by reducing the pixel-wise boundary map to a set of layer boundaries bisecting the B-scan images from the OCT scanner 18. The regions of pathology—such as SRF, focal IRF (FIRF), diffuse IRF (DIRF), drusen, reticular pseudodrusen, subretinal hyper-reflective material, intraretinal hyper-reflective foci, geographic atrophy, and retinal pigment epithelial detachments atrophic cysts, photoreceptor disruption/space; and outer retinal tabulation—are also segmented on a per-pixel basis. And the segmented regions are post-processed to remove false positives.

Further, in order to maximise performance of the segmentation steps, a range of standard image pre-processing techniques are applied including: axial motion correction; flattening of the retina; normalizing regions of high contrast; artefact recognition including shadowing; blink artefact correction; and 3D smoothing to reduce the effects of speckle.

In relation to the step of segmenting boundaries between layers of the retina, the system 10 further determines retinal layer thickness which formalises the measurement of the regions of pathology, such as diffuse IRF, and underpins the analysis of disease progression of the retina. As such, the system 10 quantifies the thickness of the retinal layers throughout the macula.

One method for layer segmentation includes graph search to find the layer boundaries following pixel-wise classification of a B-scan, which has the disadvantage of being slow to compute, taking around 2 minutes to process a single macular cube. Another method is R-Net which regresses the layer thicknesses rather than the locations of the layer boundaries. However, these systems do not take into account all the structural priors that are present in the problem. Examples of structural priors that are not taken into account by many existing systems are: continuity between layer thicknesses in consecutive B-scans and continuity between layer thicknesses in consecutive A-scans. The system 10 thus uses a-priori knowledge that layer thickness should not vary too quickly between consecutive A- and B-scans to create more robust models that hold fast variation in layer thickness in these directions as unlikely.

One layer segmentation method incorporates graph-search so that the topology of the resulting retinal layer segmentation can be guaranteed to be biologically correct (e.g. the ILM is guaranteed to appear above the IPL). This is useful because the order of the layers is preserved even in extreme disease, so segmentation models that assign non-zero probability to segmentations that include out-of-order or non-connected layer regions waste probability mass that could be assigned to biologically-plausible hypotheses. While graph-based systems are able to provide guarantees about both layer order and layer connectedness, those systems suffer from the disadvantage that their inferences are very slow to compute, especially when 2d continuity (between B-scans) is taken into account.

The system 10 uses a neural network algorithm in the form of a R-Net which provides a solution to the problem of topologically correct retinal layer segmentation, by passing individual B-scans through a cascade of two successive U-Net-like networks (S-Net and R-Net). The first network performs a pixel-wise layer segmentation (not topologically guaranteed), and the second corrects typical errors made by the first network and finally regresses the output into a sequence of layer thicknesses.

One way to incorporate continuity in layer thickness between consecutive A-scans into the design of the network is to train the network to regress the changes in layer thickness from A-scan to A-scan, rather than the layer thicknesses themselves. The activation layer may consist of a scaled tan h activation function that allows a limited range of variation from A-scan to A-scan and is biased to predict no change (which is biologically correct if the fovea is centred in the B-scans).

Since OCT scans are noisy and the locations of layer boundaries may be uncertain, the system 10 uses a Bayesian approach to layer segmentation which incorporates prior information about the likely distribution of layer thicknesses derived from population statistics. This method allows for a more accurate reconstruction of layer boundaries in noisy scans.

Gaussian processes are functional regression methods that specify a distribution over continuous functions. When used with typical kernel functions such as the RBF kernel, the distributions can encode our a-priori knowledge that layer thicknesses should not vary too quickly between consecutive A- and B-scans. The system 10 uses the model to specify a prior distribution over layer thickness (or changes in layer thickness) as a function of the A-scan and B-scan index relative to the fovea in a registered image. Then, a layer boundary segmentation image is combined with the prior to create a posterior distribution for the layer boundary which can be visualized and sampled.

Therefore, uncertainty in the layer boundary path is represented coherently, as a distribution over paths that the layer boundary could take. This is advantageous over graph-search methods for finding the layer boundary, since those methods only find a single proposal for the layer boundary, and do not represent uncertainty in the layer boundary location.

Any inference method that provides either pixel-wise layer-boundary segmentations (such as random forest classifiers or fully convolutional networks) or layer thickness estimates and their differences (such as R-Net) can be used to generate observations that can be fitted using the Gaussian process model.

The parameters of the Gaussian process prior will be derived from the population distribution of scans as well as the patient's past scans. The appropriate weighting of the population and past scan prior information is determined by cross-validation. A standard Gaussian process distribution is unimodal. However in the case of retinal layer thicknesses, there may be more than one mode: healthy patients and patients with retinal disease. To model this, the system 10 uses a hierarchical model where a disease/no disease categorical variable selects different Gaussian process priors with different parameters.

Further, the variation in layer thickness is not stationary: more variation is seen in regions of the eye that are commonly affected by disease (e.g. near the fovea). To model this, the system 10 uses a mixture of experts' model that supports non-stationary variance.

A multi-output GP can be used to model correlations between the thicknesses of the different layers, so that signal derived from one layer boundary may be used to make inferences about other layer boundaries that are correlated with the first.

The Gaussian process models are not limited to modelling continuity between consecutive A-scans. The system 10 also models continuity between consecutive B-scans using a Gaussian process with a 2d kernel function.

To provide the Gaussian process model with topological guarantees, the system 10 regresses against the output of predictor networks that measure layer thicknesses (such as R-Net) along the width of a B-scan. The system 10 may also choose to regress against the changes in layer thickness, in which case a standard zero-mean Gaussian process prior may be appropriate.

While the mixture-of-experts Gaussian process model discussed above provides support for multi-modality and non-stationarity in the distributions of retinal layer thicknesses, this model still includes simplifying conditional independence assumptions that may not reflect the true distribution. To alleviate this, the system uses a neural process model to learn the distribution of retinal layer thickness shapes. This model supports multi-modality and non-stationarity in the layer thickness distribution. It also has the advantage that it is faster to fit than the Gaussian process model when the size of the population reference set is large.

Like the Gaussian process model, this model may be used with pixel-wise layer boundary segmentation maps, or with the output of layer thickness regression networks such as R-Net, or with differenced layer thickness series.

One way to improve the performance of existing layer segmentation algorithms is to consider the information that is available in adjacent B-scans when segmenting a B-scan. To make an accurate assessment of the contents of a particular B-scan, it is helpful to look at the surrounding B-scans for context. The system 10 incorporates information from surrounding adjacent scans; one method is to inject the adjacent scans as additional input channels for input to the neural network. For example, in a U-Net segmentation model the input may have 3 input channels representing the scan to be segmented, and the two adjacent scans. The output target which the network is trained to reproduce is unchanged; the network is only trained to reproduce the segmentation for the central slice in its input.

By organising the network's input in this way, the convolutions in the lower layers of the network can learn to draw on information in B-scans adjacent to the one being segmented, to infer information that may be obscured by noise in the central B-scan.

An alternative approach for taking into account information from adjacent B-scans is for the system 10 to use 3d convolutions throughout a U-Net like network. In this approach, information derived from different B-scans, particularly B-scans that are not immediately adjacent to the scan being segmented, is more easily kept separate in the intermediate layers of the network. Furthermore, low-level features are shared across the different B-scan inputs, a property which is not present when adjacent B-scans are injected as input channels.

The method of using a 3D U-Net in the layer segmentation task may be improved by combining it with the R-Net method for creating topologically guaranteed layer segmentations. Unlike segmented pathological regions, layer boundaries exist throughout the entire retinal area. Therefore, the layer location in space can be expressed as a thickness at each point on the 2D retinal surface, rather than a compact 3-dimensional shape as in pathological region prediction. This guarantees that all layer predictions match the expected topology: an unbroken surface along the plane of the retina.

Analogously to the 2D R-Net method, the 3D R-Net starts with a segmentation system that takes the complete 3D OCT volume as input, and outputs a semantic segmentation of the entire retinal volume which indicates the layers that each voxel belongs to. This may take the form of a 3D convolutional U-Net which plays the role of the S-Net, but it is compatible with any system for segmenting the 3D OCT volume. As in 2D R-Net, this output is not guaranteed to be topologically correct. To create a topologically correct surface for each layer boundary in the retina, the segmented volume produced by the first stage is passed into a second network which aggregates the volume and outputs at each position in the plane of the retinal surface.

The second stage of the 3D R-Net method is a 3D convolutional network which takes the segmented OCT volume as input and outputs a layer thickness estimate for each layer at each point on the retinal surface. The convolutions of the network are configured so that, in the final output layer, the axis perpendicular to the frontal plane has a dimension of one, the number of channels are equal to the number of retinal layers, and the other two dimensions match the dimensions of the area of the retinal surface included by the OCT volume. This implies that the final output of the network is a 2D image with multiple channels, where each channel of each pixel can be interpreted as a layer thickness at a particular location in the retinal plane. The parameters of the convolutions and pooling layers are configured to produce the correct output dimensions. The exact configurations used may vary depending on the OCT scanner used to produce the input OCT volume.

Weights for the R-Net model are obtained by minimizing a loss function that compares ground truth layer thicknesses with the outputs from R-Net, given a set of volumetric segmentations from S-Net. The ground-truth layer thicknesses are obtained by hand-labelling of sets of consecutive B-scans by expert clinicians.

In comparison to existing methods, where layer boundaries are predicted in 2 dimensions, the 3-dimensional R-Net method has advantages in creating accurate volumetric models for retinal regions. Prediction of layer heights is performed using 3-dimensional convolutions that span adjacent slices, incorporating more information at each point to estimate layer heights. Further, as each predicted region is treated as a continuous volume, information about the surrounding 3-dimensional contour is available at each point in the plane of the retinal surface, even at the edges, reducing edge effects due to the limited volume of the OCT scan. Lastly, because the thickness regression network is trained independently of the segmentation network, the thickness regression network can be used with volume predictions from any source, including 2-dimensional layer segmentation algorithms. This gives the 3-dimensional R-Net method added flexibility: diverse methods can be used to generate volume predictions, which are converted to layer heights regardless of their source. The system 10 incorporates layer height output to produce continuous layer boundaries, which are used to guide pathological region prediction.

While large volumes of OCT scan data are easy to obtain, labelling the data to train a supervised learning system is very expensive and time-consuming. Therefore, we propose a semi-supervised learning method to leverage large amounts of unlabelled data to improve performance on the layer segmentation task. Semi-supervised learning involves learning a mapping from images to a low-dimensional embedding space, from which the content of the images can be reconstructed. When applying semi-supervised learning to a classification task, classification boundaries are learned from relatively little data on the embedding space, which is easier to do since it is low dimensional (if the representation is appropriate). Typical methods for learning such an embedding space involve training auto-encoder models such as the Variational Autoencoder (VAE), where the encoder and decoder are both deep neural networks.

While semi-supervised learning traditionally involves creating a vector representation for an entire image and learning to classify these vector representations, the reconstruction error is hard to reduce to a useful level when an entire high resolution image is considered at once (e.g. a 1024×512 B-scan from a Zeiss OCT scanner). However, in the case of layer segmentation, there is an opportunity to use a much smaller image size for training an autoencoder (e.g. 128×128), which has been shown to be feasible with VAEs.

The system 10 performs layer segmentation based on pixel-wise classifications of a B-scan followed by graph search or neural network regression to establish topologically-correct layer boundaries. The pixel-wise classification may be performed by machine learning models such as random forests or convolutional neural networks. The pixel-wise classification modules typically only consider a small patch (say 128×128) to establish context around the pixel being classified. Hence, the semi-supervised method we propose may be substituted may be substituted for the first stage in such a model cascade.

The semi-supervised learning technique may improve performance on the pixel-wise classification task because it can leverage large amounts of unlabelled data to learn a good embedding space for image patches typically found in OCT B-scans as only a 128×128 patch of context is used to classify retinal boundaries.

To improve the robustness of the representation learned by the system 10, data augmentation, such as image scaling, rotation, translation, contrast modification, and so on can be applied to the data. Furthermore, since the autoencoder should not be penalised for not reconstructing noise in the input image, a slight blur may be applied to the input patches and output targets to smooth out the effects of speckle noise.

The system 10 thus uses a combination of processes for leveraging unlabelled data for improving the performance of boundary classification using semi-supervised learning. This combination produces a pixel-wise layer segmentation map which may therefore be combined with R-Net segmentation as well as the Gaussian or neural process models described above.

In addition to layer segmentation, the system 10 performs the step of segmenting regions of pathologies such as focal IRF and drusen. In order to segment focal pathology, the system 10 uses a machine learning method based on U-Net. U-Net is an encoder-decoder network with skip connections between the corresponding layers in the encoder and the decoder. The network is trained to take raw B-scan images as inputs and produce a segmented map of focal pathology regions as output. As with layer segmentation, the network may be trained to take information in adjacent B-scan slices into account by either injecting the adjacent scans as extra channels in the input or by using 3d convolutions in a U-Net style architecture.

Additionally, the pathology segmentation network may receive supplemental channels containing layer information, generated by the layer segmentation network. In this way, layer information is used to modulate the inputs to the neural network, improving localisation of output predictions, and providing an additional method for incorporation of medical domain knowledge into the function of the neural network. Regions of pathology are restricted to specific locations: for example, Focal IRF is located above the retinal pigmented epithelium, while drusen are generally found just above Bruch's membrane. Supplying layer topology predictions to the network as extra input channels allows the network to learn associations between pathological regions and volumes delineated by layer boundaries. This provides greater specificity to pathological region predictions, as predictions are made with the relevant regions already delineated, limiting within the network where each type of pathology can plausibly occur.

The segmentation of focal pathologies returned by the U-Net may be made more accurate by filtering the continuous regions in the network using a random forest classifier. This classifier takes into account features of the segmented regions such as its size, smoothness, and location. The random forest classifier is trained to determine whether segmented regions represent real focal pathology or whether they are false positives, using the output of the trained segmentation network and the ground truth annotations as training data. When the random forest classifier predicts that a segmented region is a false positive about a certain level confidence (chosen by cross-validation), that region is eliminated from the segmentation output.

As in the layer segmentation step, in the step of focal region detection, there is an abundance of unlabelled data that should be used to improve performance on the task. In this case, rather than a semi-supervised learning approach, the system 10 uses a pre-training step on a U-Net segmentation network to make use of the unlabelled data. The U-Net is pre-trained to solve an auto-encoding problem on unlabelled data, progressively removing the skip connections in order to force the network to transmit information about retinal structure through the deeper layers of the network.

In a U-Net segmentation network that has been trained to recognise the focal region of, say, focal IRF (FIRF) in a supervised learning setting, the deeper layers of the network are expected to encode information about the global structure of the B-scan being segmented. Therefore this form of pre-training used in the system 10 should give the network an advantage in solving the supervised problem by inducing the encoder network to create an embedding space with useful features, without using the supervised training data.

Simply pre-training U-Net on unlabelled data with the usual architecture would not be effective, however, since the skip connections between the first and final layers of the network would allow the input image to be copied directly to the output layer of the network, solving the problem without inducing any useful representations in the deeper layers of the network. Therefore, the system 10 progressively removes the skip connections in the network architecture, so that representations must be created and transmitted through the deeper layers of the network. Initially the first skip connection is removed, and once the network has learnt the auto-encoding task in that configuration, the next skip connection is removed, and so on. Using this mechanism, the more abstract layers could learn about typical structures in retinal OCT B-scans, which are then in place during the supervised learning process. This will improve the model performance that results from a given amount of supervised training data.

The models used in the system 10 create predictions at each stage (layer segmentation, focal region segmentation, assessment). In all cases there is uncertainty associated with the model's output. This uncertainty is quantified and visualized to provide doctors/users with information about how confident the model is in its predictions. Feedback about model uncertainty may be presented in the form of segmentation heat-maps that are weighted by the model's confidence, visualizations of the posterior distributions in the case of GP layer segmentation, and summary signals (red/yellow/green) that aggregate model uncertainty in each of the stages of the data processing pipeline.

The training process for the models used in the system 10 combines semi-supervised learning with iterative annotation, enabling experienced clinicians to refine performance of the neural network model. Iterative annotation is a method for reducing the repetition and burden of annotation for human annotators, crucial in cases where annotation requires a high level of expert knowledge.

The system 10 uses layer predictions to further refine inference output from the model for detection of intraretinal fluid, subretinal fluid and other pathology, such as pigment epithelial detachment (PED) and subretinal hyperreflective material (SHRM). Refinement of these outputs from U-Net is performed by applying proximity rules, such as: SRF must be within a specified distance in microns from the inner boundary of the RPE; IRF must be located between the inner limiting membrane (ILM) and the RPE. Masking predictions from the Focal IRF, Diffuse IRF and SRF models provides an additional layer of quality control, preventing errant, implausible detections from influencing fluid measurements. In the system 10, these components are combined into a single model. The model may comprise operations on the input layers, such as attentional masking, or conditional logic at the output. By masking macula fluid detections using macula layer information, the network incorporates domain knowledge in the form of clearly-specified proximity rules, providing a better guarantee of robust fluid measurements than raw output from the U-Net layers alone.

The quality of detections can be further refined by detecting sources of artifacts within the OCT scan. Accuracy of measurement of the reflectivity of retinal structures is important for identifying regions of pathology and is dependent on the amount of light reaching the tissues from the OCT light source. Light can be blocked from entering deeper into the retina by structures such as the optic nerve and surrounding blood vessels, which are readily apparent in the en-face fundus image. In cases of pathology, hyperreflective foci or exudates can also block the examining light, hampering characterisation of underlying areas. The system 10 includes two methods to mitigate effects of light occlusion: firstly, by enriching training data to ensure that all light-based artifacts are well represented in the training dataset; and secondly, where necessary, by specifically detecting sources of light occlusion at the time of inference.

The system 10 derives its performance from a set of annotated OCT scans. In some cases, these scans are chosen to specifically enrich the model's performance in cases where the neural network may perform poorly, such as in conditions of light occlusion. The annotations are created by experienced clinicians, and are used as a source of domain knowledge for the neural networks (both U-Net and R-Net). Enriching the training dataset for difficult cases ensures that pathological area measurements are robust to complicating conditions, that might otherwise result in misidentification of retinal pathology.

In addition to providing examples of light occlusion at training time, the system 10 employs methods to specifically detect common causes of light occlusion. Light occlusion by blood vessels reduces the measured backscattering from structures underneath. As a result, regions of pathology such as IRF can be misidentified due to the altered light characteristics, and areas of very low backscattering can be mistaken for cysts, where fluid is expected to have low reflectivity. Therefore, to mitigate this effect and to further improve accuracy of detection of IRF regions in macular pathology, an additional method applied as part of the system 10 is the detection of blood vessels in the OCT scan. Blood vessels are detected either in the en-face fundus image, by their cross section in OCT slices, or by their appearance in 3-dimensions in the aggregated OCT scan. Once blood vessels are located, they are either used as an additional input to the neural network alongside OCT scan data, or as a mask on inferences. By using blood vessel locations to mask IRF detections, the system 10 ensures that any detections resulting solely from light artifacts caused by blood vessels are removed. Thus, specifically targeting light artifacts caused by blood vessels adds an additional level of quality control.

The datasets available to train predictive models for patient outcomes and the effects of interventions are relatively small compared to those available for training models for inference over B-scans, since an entire patient time-series may represent only a single training example. Therefore, the system 10 incorporates mechanisms for feature extraction on segmented OCT scans, so that machine learning approaches for prediction can work without requiring representation learning.

Features of the retinal layers include: thickness statistics; layer integrity; continuity; contour; smoothness/roughness; gradients; location of abnormal thickening relative to fovea; and neural process representation of the layer.

Features of the regions of pathology (fluid, drusen, etc.) include: size; shape; location; and count.

Features of change from scan to scan include: movement of fluid; areas where new fluid has accumulated; areas where fluid has gone away; and differences; movement of layer in representation space.

Quantifying fluid volume includes: regions—volume; changes in layer thickness from normal; and diffuse IRF—differences in layer thicknesses minus regions.

Further, rather than express all features of patients' scans in absolute terms (absolute layer thickness, fluid volume, etc.), the system 10 represents them as percentiles in population distributions. The reference distributions from which the percentiles are drawn are calculated from the population of scans.

The system 10 performs dimensionality reduction on the above features extracted from individual scans as well as features extracted from the entire patient history. This may use classical methods such as PCA.

As mentioned, the system 10 outputs an assessment which may be one of a selection of optimal treatment regimens for individual patients based on the features of their OCT scan and treatment history. To this end, the patient's treatment history and the features extracted in the previous stage to train machine learning models are used to predict the outcomes of treatment regimens for patients. These models may include classical machine learning models such as decision trees, as well as neural network methods that can respond to the variable-length nature of a patient's treatment history such as RNNs. The models take into account features of the entire treatment history such as: time between treatments; features of disease at each time point; past treatments used; past treatment regimens (protocols) used; treatment history in the other eye, etc.

The training framework for the models will either take the form of a supervised learning problem (predict the outcome for the patient given this treatment history), or as an off-policy reinforcement learning problem, where the model learns a value function that estimates the usefulness of each treatment option in a given scenario.

In both cases, the goal is to estimate the causal effect of a treatment option, so that the optimal treatment can be chosen. To do this, any potential confounders (attributes of the patient that the doctor considers when prescribing treatment) will be identified, measured, and added to the patient history for the models to take into account. This way, a propensity score adjustment can be made and the causal effect of treatment can be estimated. Then, the optimal treatment can be selected by optimising the predicted effect of each treatment option.

The feature extraction component of the system 10 will enable the construction of predictive models in a low data scenario. However, once the system 10 is deployed, more patient treatment time-series will be collected. Once sufficient data becomes available, the system 10 will further include a representation learning approach to the time-series prediction problem outlined above. This will involve training deep neural networks end-to-end in the reinforcement learning setting to perform feature extraction on the raw OCT data such that the learned features have predictive value for the patients' future health outcomes. These networks will be multi-modal in that they will also take into account inputs such as patient demographics and treatment history. This approach has the potential to learn new features of OCT images that are clinically relevant, but are not known in a rule-based feature extraction system.

Figure 3:
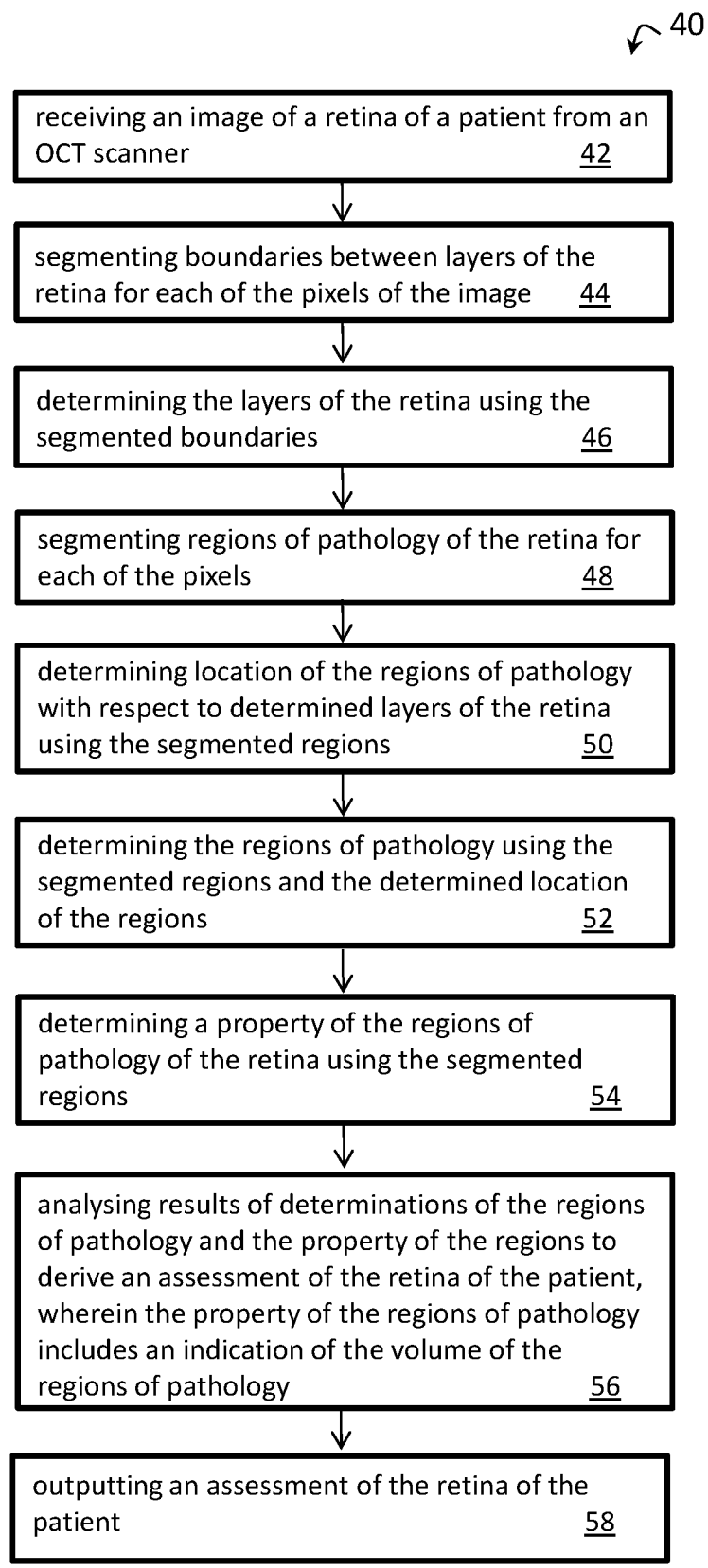
FIG. 3 is a flow chart summarising a method of analysing images of a retina according to an embodiment of the present invention.

Referring now to FIG. 3, there is shown a method 40 of analysing images of a retina captured by an Optical Coherence Tomography (OCT) scanner. The method 40 uses a processor to implement the steps of: receiving 42 images of a retina of a patient from an OCT scanner, the image having a plurality of pixels; segmenting 44 boundaries between layers of the retina for each of the pixels; determining 46 the layers of the retina using the segmented boundaries; segmenting 48 regions of pathology of the retina for each of the pixels; determining 50 a location of the regions of pathology with respect to the determined layers of the retina using the segmented regions; determining 52 the regions of pathology using the segmented regions and the determined location of the regions; determining 54 a property of the regions of pathology of the retina using the segmented regions; analysing 56 results of determinations of the regions of pathology and the property of the regions to derive an assessment of the retina of the patient, wherein the property of the regions of pathology includes an indication of the volume of the regions of pathology; and outputting 58 the assessment of the retina of the patient.

The system 10 further provides visualisations to clearly explain the steps involved in the measurement of volumes, and generation of recommendations for treatment. Detected areas of pathology are drawn as heat-maps onto a two-dimensional representation of slices through the OCT scan. An en-face view of the macula is shown, including all detected fluid in the OCT scan, presented in a single image. In this en-face view, the intensity of colour of depicted fluid areas is proportional to the thickness of the detected fluid. The system 10 contains the facility to accurately overlay drawn areas of pathology onto a fundus image, either acquired using a scanning laser ophthalmoscope (SLO), or by integration of the 3D tomogram along depth. In cases where an SLO fundus image is unavailable, integration by depth is performed using pixel intensity along the surface of any of the detected layers, such as ILM or RPE. In this manner, the en-face image created from the OCT scan follows the shape of the macula. This has an advantage over display systems that rely on a single format for the fundus image: the system 10 leverages the high-resolution LSO image if it exists, but also guarantees that a lower resolution fundus image generated from the OCT scan can be made available in cases where the LSO image is missing, corrupted or inadequate for display.

Pathological areas are labelled according to a colour-code, enabling clinicians to easily distinguish the different types of pathology. To ensure that labelled areas are always highly visible, the most intense grades of the heat-map are near-white, and lower grades are a light shade of the respective colour assigned to that pathology type. As heat-maps produced by U-Net for pathological region detection commonly have their most intense regions in the centre, and less intense regions on the outside, the choice of colour map results in labelled areas that are near-white in the centre, and strongly coloured on the outside edges. This has an advantage over flat colour, as the heat-maps created using this method can be more easily discerned, even in cases where the area of pathology is small, or where the image is reduced in size and displayed alongside other elements. The coloured outside edges ensure that labels for the different types of pathology can be readily distinguished.

The software 16 will also incorporate an interface for navigating 3-dimensional display of labelled areas of pathology within the entire volume of the OCT scan. Where 2-dimensional slices are presented, their location within the context of the OCT scan will be clearly marked, through the use of indicator lines drawn on a representation of the entire OCT scan, such as the en-face image. The system also includes methods for creating a 3-dimensional volumetric shape for display from the output of the U-Net model, by applying a threshold to 3-dimensional heat-maps, and coercing the resulting 3-dimensional mask to a geometric surface. A surface is created by generating an array of triangular polygons at the outermost of the thresholded heat-map, using performance optimised methods including but not limited to the following: calculation of the convex hull, 3-dimensional Delaunay triangulation, and 3-dimensional model refinement, with limits for polygon count and minimum angle of vertices. The surfaces constructed via these methods allow the labelled regions to be viewed clearly from all sides, with the appearance of solid objects. After converting the pathological region predictions data to a 3-dimensional surface, the pathological areas are made available for viewing from any angle, in combination with a set of controls for rotation, panning and zoom. Compared with existing OCT scan software, 3-dimensional display gives users greater control over the viewing angle, allowing much more freedom than the standard 3 anatomical axes. The ability to freely rotate the viewing angle eases interpretation, especially in cases where pathological regions of different classes occlude each other in static, 2-dimensional representations.

In addition, it will be appreciated by those persons skilled in the art that further aspects of the method 40 will be apparent from the above description of the system 10. Further, the persons skilled in the art will also appreciate that at least part of the method 40 could be embodied in software (e.g. program code) that is implemented by the processor 12 configured to control the apparatus for analysing images of a retina. The software 16 could be supplied in a number of ways, for example of a tangible computer readable medium, such as a disc, or in the memory 14 as shown in FIG. 1.

Those skilled in the art will also appreciate that the invention described herein is susceptible to variations and modifications other than those specifically described. It is to be understood that the invention includes all such variations and modifications.

What is claimed is:

1. A method of analysing images of a retina captured by an Optical Coherence Tomography (OCT) scanner, the method using a processor configured to implement the steps of:
receiving an image of a retina of a patient from an OCT scanner, the image having a plurality of pixels;
segmenting boundaries between layers of the retina for each of the pixels;
determining the layers of the retina using the segmented boundaries;
segmenting regions of pathology of the retina for each of the pixels;
determining a location of the regions of pathology with respect to the determined layers of the retina using the segmented regions;
determining the regions of pathology using the segmented regions and the determined location of the regions;
determining a thickness of the layers of the retina using the segmented boundaries in a neural network model;
determining the thickness of the layers of the retina using a distribution of layer thicknesses derived from known layer thicknesses of a population;
determining a property of the regions of pathology of the retina using the segmented regions;
analysing results of determinations of the regions of pathology and the property of the regions to derive an assessment of the retina of the patient,
wherein the property of the regions of pathology includes an indication of the volume of the regions of pathology; and
outputting the assessment of the retina of the patient.

2. The method of claim 1, further including storing the image of the retina of the patient in a memory, receiving a subsequent image of the retina of the patient, and storing the subsequent image of the retina of the patient in the memory.

3. The method of claim 2, further including storing the assessment in a memory, and comparing the assessment in the memory with a subsequent assessment of the subsequent image of the retina of the patient derived using the method of claim 1 to derive a progress assessment for the patient.

4. The method of claim 2, further including transforming the image and the subsequent image of the retina to normalise parameters of the image and the subsequent image.

5. The method of claim 4, further including registering the image and the subsequent image of the retina into a standard coordinate space.

6. The method of claim 5, further including aligning the image and the subsequent image into the standard coordinate space using a fundus image of blood vessels of the retina received from the OCT scanner, wherein the blood vessels have fixed locations in the standard coordinate space.

7. The method of claim 5, further including classifying, using a fovea finding classifier, each of the pixels of the image into fovea and retina classifications; and identifying the centre of the fovea of the retina in the image based on results of the fovea and retina classifications of the pixels.

8. The method of claim 7, further including aligning the image and the subsequent image into the standard coordinate space using the centre of the fovea.

9. The method of claim 1, further including further determining the thickness of the layers of the retina using a distribution of layer thickness shapes derived from known layer thickness shapes of a population.

10. The method of claim 1, further including segmenting boundaries between layers using adjacent B-scans of images of the retina received from the OCT scanner.

11. The method of claim 1, wherein the regions of pathology include focal regions of pathology and non-focal regions of pathology.

12. The method of claim 11, wherein the focal and non-focal regions of pathology include: subretinal fluid SRF; focal intraretinal fluid (FIRF); diffuse intraretinal (DIRF); drusen; reticular pseudodrusen, subretinal hyper-reflective material, intraretinal hyper-reflective foci, geographic atrophy; retinal pigment epithelial detachments; polypoidal choroidal vasculopathy; atrophic cysts; photoreceptor disruption/space; and outer retinal tubulation.

13. The method of claim 11, further including determining a layer topography of the retina using the segmented boundaries and comparing the layer topography of the retina to an expected layer topography of a retina without any regions of pathology.

14. The method of claim 13, further including determining a distribution of the non-focal regions of pathology in the retina by combining the expected layer topography with the segmented regions of pathology.

15. The method of claim 1, wherein the layers of the retina include: retinal pigment epithelium layer; layer of inner and outer segments; outer limiting layer; outer nuclear layer; outer plexiform layer; inner nuclear layer; inner plexiform layer; ganglion layer; layer of nerve fibres; and inner limiting layer.

16. The method of claim 1, wherein the property of the regions of pathology further includes: size of the regions; shapes of the regions; location of the regions; and a count of the regions.

17. A system for analysing images of a retina, the system including:
- an Optical Coherence Tomography (OCT) scanner configured to capture images of a retina, each of the images having a plurality of pixels;
- a processor in data communication with the OCT scanner;
- a memory; and
- software resident in the memory accessible to the processor, the software including a series of instructions executable by the processor to configure the processor to:
- receive an image of a retina of a patient from the OCT scanner;
- segment boundaries between layers of the retina for each of the pixels;
- determine the layers of the retina using the segmented boundaries;
- segment regions of pathology of the retina for each of the pixels;
- determine a location of the regions of pathology with respect to the determined layers of the retina using the segmented regions;
- determine a thickness of the layers of the retina using the segmented boundaries in a neural network model;
- determine the thickness of the layers of the retina using a distribution of layer thicknesses derived from known layer thicknesses of a population;
- determine the regions of pathology using the segmented regions and the determined location of the regions;
- determine a property of the regions of pathology of the retina using the segmented regions;
- analyse results of determinations of the regions of pathology and the property of the regions to derive an assessment of the retina of the patient,
- wherein the property of the regions of pathology includes an indication of the volume of the regions of pathology; and
- output the assessment of the retina of the patient.

* * * * *